United States Patent [19]
Cook et al.

[11] Patent Number: 6,162,952
[45] Date of Patent: Dec. 19, 2000

[54] PRODUCTION OF MERCAPTANS USING HETEROGENEOUS ACIDIC CATALYSTS

[75] Inventors: Charles M. Cook, Williamsville; David E. Albright, Grand Island; Michael C. Savidakis, Niagara Falls, all of N.Y.

[73] Assignee: Occidental Chemical Corporation, Dallas, Tex.

[21] Appl. No.: 09/313,490

[22] Filed: May 17, 1999

Related U.S. Application Data

[63] Continuation-in-part of application No. 09/003,231, Jan. 6, 1998, abandoned.

[51] Int. Cl.$^7$ .................................................. C07C 319/04
[52] U.S. Cl. .................................. 568/72; 568/69; 568/61
[58] Field of Search .................................. 568/61, 69, 72

[56] References Cited

U.S. PATENT DOCUMENTS

| | | |
|---|---|---|
| 2,426,646 | 9/1947 | Schulze . |
| 2,592,089 | 4/1952 | Warner . |
| 4,582,939 | 4/1986 | Perozzi et al. ............................ 568/72 |
| 5,453,544 | 10/1995 | Giacobbe ................................. 568/72 |

*Primary Examiner*—Jean F. Vollano
*Attorney, Agent, or Firm*—Richard D. Fuerle; Anne E. Brookes

[57] ABSTRACT

Disclosed is a method of making a mercaptan by reacting hydrogen sulfide with an olefin in the presence of a heterogeneous acidic catalyst. The catalyst can be made by calcining a mixture of a hydroxide, such as $Zr(OH)_4$ or $Ti(OH)_4$, with an acidic site donor, such as $H_2SO_4$, $(NH_4)_2SO_4$, or $WO_3$.

20 Claims, No Drawings

12# PRODUCTION OF MERCAPTANS USING HETEROGENEOUS ACIDIC CATALYSTS

This application is a continuation-in-part of application Ser No. 09/003,231, filed Jan. 06, 1998, now abandoned.

BACKGROUND OF THE INVENTION

This invention relates to a method of making mercaptans. In particular, it relates to reacting hydrogen sulfide with an olefin in the presence of a heterogeneous acidic catalyst.

Mercaptans can be made by reacting olefins with hydrogen sulfide in the presence of a heterogeneous catalyst. Catalysts that have been used for this reaction include acidic clays such as acid washed montmorillonite clay (U.S. Pat. No. 2,950,324), promoted silicas (U.S. Pat. No. 2,951,875), zeolites (U.S. Pat. Nos. 4,102,931, and 5,453,544), doped acidic alumina (EU 0354460B1), and acidic ion exchange resins (CZECH 185469B1, U.S. Pat. No. 4,565,893, and U.S. Pat. No. 4,582,939).

The quality qf the catalyst is measured by the percent conversion of the olefin feed into a product and by the selectivity (i.e., the yield of the desired product). The best catalysts appear to be the acidic ion exchange resins. Optimized, they give conversions of over 95% and selectivities over 90% at hydrogen sulfide to olefin weight ratios of greater than or equal to 3 to 1 at 150 psig and 45 to 75° C. with a throughput of 0.6 grams of olefin per mL of catalyst per hour. Unfortunately, acidic ion exchange resins begin to degrade at 100° C. and substantially decompose at temperatures of 140° C. Since the reaction of an olefin with hydrogen sulfide is highly exothermic, this imposes significant constraints on the use of this type of catalyst.

SUMMARY OF THE INVENTION

We have discovered that certain heterogeneous acidic catalysts are excellent catalysts for the reaction of olefins with hydrogen sulfide to produce mercaptans. The catalysts used in this invention are significantly superior to the best existing catalysts for this reaction, the acidic ion exchange resins. The catalysts readily give nearly complete conversion of the olefin feed, but can also be optimized to give a mercaptan product which contains little or no sulfide byproducts or olefin oligomers. The selectivity of tie catalysts is over 95% and the conversion is also over 95% at a hydrogen sulfide to olefin weight ratio of 2 to 1 at 150 psig and 130° C. The yield is excellent, which is especially unexpected because previous work has shown that heterogeneous acidic catalysts efficiently promote olefin oligomerization (see U.S. Pat. Nos. 5,191,139; 5,113,034; and 5,304, 696). The throughput, at 4 grams of olefin per mL of catalyst per hour, is significantly greater than the throughput of the acidic ion exchange resin catalysts.

The catalysts are stable to at least 200° C. and can be regenerated by heating to higher temperatures for short periods of time. They are easier to use industrially than the acidic ion exchange resins because they can be extruded into different shapes and sizes to improve the flow and loading. Also, while the acidic ion exchange resins typically must be loaded as aqueous slurries containing up to 50% solids, the catalysts of this invention can be loaded directly into the reactor.

DESCRIPTION OF THE PREFERRED EMBODIMENTS

In the process of this invention, an olefin is reacted with hydrogen sulfide in the presence of a heterogeneous acidic catalyst. The olefin must be a gas, a liquid, or a liquefied solid.

The olefins are unsaturated hydrocarbons, where the unsaturation can be in any position. They can be mono-unsaturated, di-unsaturated, or poly-unsaturated, but are preferably mono-unsaturated as the resulting mercaptans have more commercial applications. If 2 or more unsaturated groups are present, each unsaturated group will form a mercaptan. The olefin must contain at least 2 carbon atoms and preferably contains 2 to 18 carbon atoms as higher olefins are of little commercial value. Examples of suitable olefins include dodecene, tetrapropylene (a mixture of mono-unsaturated oligomers made by reacting propylene), nonene or tripropylene, isobutylene, and propylene. Tetrapropylene, isobutylene, and nonene are preferred as they are commercially more important.

The catalyst used in this invention has the form M/X, where the M portion is titanium dioxide ($TiO_2$), zirconium oxide ($ZrO_2$), or a mixture thereof and the X portion is formed from an oxide, acid, or acid salt of sulfur, phosphorus, or a Group 3 to 12 transition metal (using new periodic table). Examples of oxides and acidic anions of acid salts that can be used to form the X portion include $SO_4^-$, $SO_4^=$, $PO_4^-$, $PO_3^=$, $PO_3^-$, $WO_3$, $WO_4^-$, $WO_4^=$, $MoO_3$, $MoO_4^-$, and $MoO_4^=$. The X portion of the catalyst is preferably $SO_4$ as those catalysts have more acid equivalence and therefore promote a more rapid reaction. In the M/X formula, about 0.1 to about 10 wt % should consist of X (calculated as $SO_3$ or the equivalent), wh ere the percentage is based on the total catalyst weight, as a lower portion of X is less effective and a greater portion of X will reduce the activity of the catalyst. Preferably, the proportion of X is about 2.1 to about 4.7 wt % of the total catalyst weight.

Alternatively, the catalysts used in this invention, commonly known as "solid acid catalysts," can be described as being the calcination reaction product of a mixture of a metal hydroxide with an acidic site donor. Examples of suitable metal hydroxides include $Ti(OR)_4$, $Zr(OH)_4$, $Hf(OH)_4$, $Nb(OH)_5$, $Ta(OH)_5$, $La(OH)_5$, $Si(OH)_4$, and mixtures thereof. The preferred metal hydroxides are $Ti(OH)_4$, $Zr(OH)_4$, and mixtures thereof because catalysts made from them have been found to work well. The metal hydroxide is about 51 to about 99 wt % of the mixture weight, and preferably is about 80 to about 96 wt % of the mixture weight.

The acidic site donor is a compound that can place oxy anions in the matrix formed during calcination. The oxy anions comprise an element that is at least divalent bonded to at least two oxygen atoms. Examples of suitable acidic site donors include $H_2SO_4$, $(NH_4)_2SO_4$, $(NH_4)HSO_4$, $SO_3$, $WO_3$, $H_2WO_4$, $(NH_4)_2WO_4$, $W(NO_3)_6$, $H_3PO_4$, $(NH_4)_3PO_4$, $(NH_4)_2HPO_4$, $(NH_4)H_2PO_4$, and mixtures thereof preferred acidic site donors are $H_2SO_4$, $(NH_4)_2SO_4$, $WO_3$, and mixtures thereof because catalysts made from them have been found to work well. The acidic site donors are about 1 to about 49 wt % of the weight of the mixture used to form the catalyst and are preferably about 4 to about 20 wt % of that mixture weight. For example, about 5 to about 10 wt % $SO_4$ is preferably present in the catalyst when the metal hydroxide is $Zr(OH)_4$.

The catalyst may contain a small amount of a dopant to increase its stability and extend its lifetime. Examples of dopants that can be used include $Y_2O_3$, $CaO$, $La_2O_3$, and $SiO_2$. The preferred dopants are $La_2O_3$ and $SiO_2$ as they work well. Up to 20 wt % (calculated as the metal ion) of a dopant can be included in the catalyst, based on total catalyst weight. The preferred amount of dopant is about 0.1 to about 7 wt %, based on the catalyst weight.

The preparation of the heterogeneous acidic catalysts used in this invention is known and some of them are commercially available; they have been used to catalyze other types of reactions. See, for example, the following literature, herein incorporated by reference: Xuemin Song et al., "Sulfated Zirconia Based Strong Acid Catalyst: Recent Progress," Catal. Rev. Sci. Eng. 38, 329–412 (1996); K. Tanabe et al., "Design of Sulfur Promoted Solid Superacid Catalyst," Successful Design of Catalysts, 99–110, Elsevier Science Publications, T. Inui, editor, 1988; Kazushi Arata, "Solid Superacids," Advances in Catalysis, 37 (1990), 165–211, especially pages 177–204; Tsutomu Yamaguchi, "Recent Progress in Solid Superacids," Applied Catalysis, 61 (1990), 1–25, especially pages 12–23; and M. Misono et al., "Solid Superacid Catalysts," Chemtech, November 1993, 23–29, especially pages 24–25. The catalysts have also been used for the oligomerization of olefins (e.g., U.S. Pat. Nos. 5,191,139; 5,113,034; and 5,304,696), the alkylation of phenol (e.g., U.S. Pat. Nos. 4,236,033 and 5,304,688), and the akylation of aromatics with olefins (e.g., U.S. Pat. Nos. 5,243,115; 5,396,011; 5,516,954; and 5,563,311). The catalysts have been used for reactions which traditionally use Bronstead acid-Lewis acid combinations as catalysts.

The catalysts can be made by contacting the solid metal hydroxide with a solution of the acidic site donor, drying, and repeating this procedure until the desired amount of acidic site donor has been absorbed onto the solid metal hydroxide. Alternatively, the acidic site donor can be precipitated onto the solid metal hydroxide or dry acidic site donor and solid metal hydroxide can be mixed. The mixture is calcined in air, typically at about 300 to about 900° C., and preferably at about 400 to about 700° C. for up to 5 hours or more, the time and temperature of calcination depending upon the particular catalyst. Calcining for too long or at too high a temperature can deactivate the catalyst. During calcining, the acidic site donor reacts with the metal hydroxide to form various complicated oxygen-bridged matrices. For example, the catalyst sulfated zirconia can be made by reacting $(NH_4)_2SO_4$ with $Zr(OH)_4$ at temperatures of about 460 to about 900° C. The product of this reaction is not $Zr(SO_4)_2$. The actual structure of the product is not known, but it is believed to be a network which could contain structures such as:

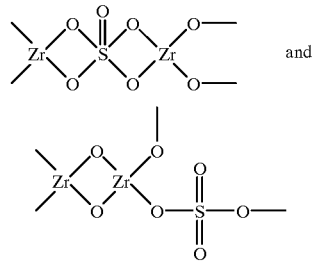

and

The resulting catalyst is a solid that has enhanced acidity. It preferably has a Hammett Acid Strength (—HO) of at least 11.9 (i.e., at least as acidic as sulfuric acid). The catalyst should have a surface area of at least about $5 m^2/g$ as catalysts have a less surface area produce lower conversion. Preferably, the catalyst has a surface area of about 70 to about 100 $m^2/g$. For a more detailed description of the catalysts used in this invention see, for example, the article, "Solid Superacids," by K. Tanabe et al. in *Heterogeneous Catalysis*, G. Ertl et al. (Wiley VCH, 1997), and U.S. Pat. Nos. 4,918,041; 4,956,518; 5,019,671; 5,310,868; 5,321,197; 5,345,028; 5,396,011; and 5,516,954. Generally, catalysts that work in isomerization reactions will work in the thiolation reactions of this invention.

The reaction between the olefin and the hydrogen sulfide can occur between 0 and 140° C. Higher temperatures may result in the decomposition of the product and at lower temperatures the reaction is slow; preferably, a temperature of about 80 to about 120° C. is used. The molar ratio of the hydrogen sulfide to the olefin should be at least 1.0 to ensure complete reaction of the olefin. Lower ratios can be used if one wishes to produce a sulfide product instead of a mercaptan product. Preferably, the molar ratio is 1.0 to about 3 as ratios over 3 are unnecessary and waste hydrogen sulfide. Gaseous hydrogen sulfide and gaseous, liquid or liquefied solid olefin are passed over the solid catalyst. About 2 to about 8 g of the olefin should be used per gram of the catalyst per hour.

The following examples further illustrate this invention.

EXAMPLE 1

In this example, the reactor consisted of a ½ inch (1.3 cm) diameter 316 stainless steel (ss) tube either 14 inches (35.6 cm) or 36 inches (91.4 cm) long fitted with a catalyst support screen and internal thermocouple. The reactors were either surrounded by an electric heating mantle or by a 1 inch (2.54 cm) diameter 316 ss tube through which glycol was pumped. The volume and weight of catalyst used were recorded for each catalyst charge. The liquid olefin feedstock was metered into a flowing stream of $H_2S$. In some cases, a preheater was employed to heat up the reactants prior to entering the catalyst reactor. The $H_2S$ flow rate was controlled to conduct a series of tests in the range of 0.5 to 20 molar equivalents. The reactor pressure was controlled by an outlet control valve to conduct a series of experiments in the range of 0 to 180 psig (0 to 1.2 MPa). The reaction products were collected in a stainless steel receiver. Samples from various operating conditions were analyzed by gas chromatography (GC) to determine mercaptan, sulfide, and unreacted olefin content. Hydrogen sulfide and gaseous olefin were passed over 34 g of the catalyst. The catalyst consisted of 96.4 wt % $ZrO_2$/3.4 wt % $SO_4$ (calculated as $SO_3$) available from MEI as "X20682/01" sulfated zirconia or from Engelhard as sulfated zirconia. The following table gives the reaction conditions and the results.

| Catalyst | Temperature (° C.) | Feed Rate (g/min) | H₂S Feed (mL/min) | Pressure (psig) | H₂S/Olefin (molar ratio) | GC area % Olefin | GC area % Mercaptan | GC area % Sulfide | Rate (g/mL catalyst/hr) | Rate (lb/lb catalyst/hr) |
|---|---|---|---|---|---|---|---|---|---|---|
| Tripropylene To Tertiary Nonyl Mercaptan | | | | | | | | | | |
| Amberlyst 15 (1) | 95 | 0.649 | 844 | 95 | 9.8 | 6.1 | 92.8 | 1.2 | 0.927 | 1.30 |
| ZrO₂/SO₄ | 130 | 1.01 | 536 | 101 | 3.0 | 4.7 | 88.1 | 7.2 | 1.92 | 1.74 |
| Tetrapropylene To Tertiary Dodecyl Mercaptan | | | | | | | | | | |
| Amberlyst 15 (1) | 113 | 1.66 | 524 | 155 | 2.4 | 0.0 | 100.0 | 0.0 | 1.00 | 1.38 |
| Zeolite (2) | 119 | 0.055 | 994 | 140 | 13.6 | 8.6 | 91.4 | 0.0 | 0.79 | 1.49 |
| ZrO₂SO₄ | 130 | 1.1 | 880 | 150 | 5.8 | 0 | 100 | 0 | 2.10 | 1.89 |
| ZrO₂SO₄ | 130 | 1.1 | 812 | 160 | 5.4 | 0 | 100 | 0 | 2.10 | 1.89 |
| ZrO₂SO₄ | 132 | 2.2 | 1023 | 147 | 3.4 | 0.3 | 99.7 | 0 | 4.13 | 3.73 |
| ZrO₂SO₄ | 133 | 2.2 | 1023 | 142 | 3.4 | 0.4 | 99.6 | 0 | 4.13 | 3.73 |
| ZrO₂SO₄ | 136 | 2.2 | 302 | 155 | 1.0 | 11.2 | 88.8 | 0.0 | 4.13 | 3.73 |
| ZrO₂SO₄ | 137 | 2.2 | 598 | 155 | 2.0 | 0.4 | 99.6 | 0.0 | 4.13 | 3.73 |

(1) Acidic ion exchange resin sold by Rohm & Haas.
(2) Sold by Zeolyst as "CBV-400."

Conditions were not optimized for the tripropylene experiment. Nevertheless, this experiment shows that for the heterogeneous acidic catalyst converted about twice as much tripropylene as did the acidic ion exchange resin and at a significantly higher rate. The experiments with tetrapropylene show that the heterogeneous acidic catalyst had a rate of conversion several times the rate of the acidic ion exchange resin.

EXAMPLE 2

Pilot reactions were conducted in a 316 ss jacketed tube (6'×1" ID) packed with approximately 500 cc catalyst supported on a pad of stainless steel mesh. A four point thermocouple was inserted from the bottom of the reactor to measure a temperature profile at approximately one foot intervals. A single point thermocouple was used to measure temperature at near the top of the catalyst bed. Hot oil controllable between 80 and 590° F. was used in the reactor jacket to control reaction temperature.

Liquified isobutene was fed to the bottom of a hot oil jacketed vaporizer (6'×1" ID) via a calibrated metering pump at 16 to 32 mL/min. Gaseous hydrogen sulfide was fed to the bottom of the vaporizer via a calibrated mass flow controller at 12 to 55 standard liters/minute (SLM). The vaporized isobutene and hydrogen sulfide mixture leaving the top of the vaporizer was fed to the top of the reactor (down flow operation).

The catalytic reaction was highly exothermic and could be monitored with the multipoint thermocouples in the reactor. The products leaving the bottom of the reactor were cooled in a heat exchanger and fed to a product receiver. A chilled reflux condenser on the product receiver outlet minimized product loss which could occur with the excess hydrogen sulfide flow. Reactor system pressure was controlled using a back pressure regulator on the hydrogen sulfide exit gas.

Surprisingly, the sulfated zirconia catalysts gave higher selectivities for the preparation of tertiary butyl mercaptan (TBM) than either the Engelhard "G-62 Filtrol" clay or the UOP "Y84" decatonized zeolite. And, unlike the clay and the zeolite, the sulfated zirconia catalysts gave little or no diisobutylene (DIB):

| Catalyst | TBM Selectivity (%) | DIB (%) |
|---|---|---|
| Engelhard "G-62 Filtrol" Clay | 95 | 0.9 |
| UOP "Y84" decatonized zeolite | 96 | 0.4 |
| Engelhard Sulfated Zirconia | 97 | 0.05 |
| Diluted Engelhard Sulfated Zirconia | 98+ | 0.00 |

We claim:

1. The reaction of a gaseous hydrogen sulfide with a gaseous, liquid, or liquefied olefin to produce a mercaptan catalyzed by a catalyst having the form M/X, made by
   (A) preparing a mixture of
      (1) about 51 to about 99 wt % of a hydroxide of titanium, zirconium, hafnium, niobium, tantalum, lanthanum, or a mixture thereof, which forms the M portion of said catalyst; and
      (2) about 1 to about 49 wt % of an acid or acid salt of sulfur, an acid or acid salt of phosphorus, or an acid or acid salt of a Group 3 to 12 transition metal and mixtures thereof, which forms the X portion of said catalyst; and
   (B) calcining said mixture.

2. The reaction of claim 1 wherein said olefin is mono-unsaturated and contains 2 to 18 carbon atoms.

3. The reaction of claim 1 wherein said mixture is calcined at a temperature of about 300 to about 900° C.

4. The reaction of claim 3 wherein said olefin is tetrapropylene.

5. The reaction of claim 3 wherein said olefin is isobutylene.

6. The reaction of claim 3 wherein said olefin is nonene.

7. The reaction of claim 1 wherein said hydroxide is Zr(OH)₄, Ti(OH)₄, or a mixture thereof.

8. The reaction of claim 7 wherein said X portion is made from sulfuric acid or a salt thereof.

9. The reaction of claim 1 wherein said acid or acid salt is selected from the group consisting of $H_2SO_4$, $(NH_4)_2SO_4$, $(NH_4)HSO_4$, $SO_3$, $WO_3$, $H_2WO_4$, $(NH_4)_2WO_4$, $W(NO_3)_6$, $H_3PO_4$, $(NH_4)_3PO_4$, $(NH_4)_2HPO_4$, $(NH_4)H_2PO_4$, and mixtures thereof.

10. The reaction of claim 1 where said hydroxide is Ti(OH)₄, Zr(OH)₄, or a mixture thereof.

11. The reaction of claim 1 wherein said catalyst has a surface area of 70 to 100 m²/g.

12. The reaction of claim 1 wherein about 2 to about 8 g of said olefin are used per gram of said catalyst hour.

13. The reaction of claim 1 wherein said catalyst includes about 0.1 to about 7 wt % of a dopant of $La_2O_3$ or $SiO_2$.

14. A method of making a mercaptan comprising reacting hydrogen sulfide with a mono-unsaturated olefin having 2 to 18 carbons atoms in a molar ratio of said hydrogen sulfide to said mono-unsaturated olefin of at least one, in the presence of a catalyst having a Hammett Acid Strength (—HO) of at least 11.9, made by
   (A) preparing a mixture of
      (1) about 80 to about 96 wt % of a hydroxide selected from the group consisting of $Zr(OH)_4$, $Ti(OH)_4$, and mixtures thereof; and
      (2) about 4 to about 20 wt % of an acidic site donor selected from the group consisting of $H_2SO_4$, $(NH_4)_2SO_4$, $(NH_4)HSO_4$, $SO_3$, $WO_3$, $H_2WO_4$, $(NH_4)_2WO_4$, $W(NO_3)_6$, $H_3PO_4$, $(NH_4)_3PO_4$, $(NH_4)_2HPO_4$, $(NH_4)H_2PO_4$, and mixtures thereof, and
   (B) calcining said mixture at a temperature of about 300 to about 900° C.

15. A method according to claim 14 wherein said acidic site donor is selected from the group consisting of $H_2SO_4$, $(NH_4)_2SO_4$, $WO_3$, and mixtures thereof.

16. A method according to claim 14 wherein said olefin is tetrapropylene.

17. A method according to claim 14 wherein said olefin is isobutylene.

18. A method according to claim 14 wherein said olefin is nonene.

19. A method of making a mercaptan comprising reacting hydrogen sulfide with tetrapropylene, isobutylene, or nonene at a molar ratio of hydrogen sulfide to tetrapropylene, isobutylene, or nonene of 1.0 to about 3, in the presence of a catalyst made by
   (A) preparing a mixture of
      (1) about 80 to about 96 wt % of a hydroxide selected from the group consisting of $Zr(OH)_4$, $Ti(OH)_4$, and mixtures thereof; and
      (2) about 4 to about 20 wt % of an acidic site donor selected from the group consisting of $H_2SO_4$, $(NH_4)_2SO_4$, $WO_3$, and mixtures thereof; and
   (B) calcining said mixture at a temperature of about 300 to about 900° C.

20. A method according to claim 19 wherein said catalyst is made by calcining at a temperature of about 400 to about 700° C.

* * * * *